United States Patent [19]

Beaudouin et al.

[11] 4,145,721
[45] Mar. 20, 1979

[54] PHOTOSENSITIVE SELF SCAN ARRAY WITH NOISE REDUCTION

[75] Inventors: Pierre L. Beaudouin, Dammarie les Lys; Pierre Debord, Vence, both of France

[73] Assignee: International Business Machines Corporation, Armonk, N.Y.

[21] Appl. No.: 764,100

[22] Filed: Jan. 31, 1977

[30] Foreign Application Priority Data

Jun. 24, 1976 [FR] France .................... 76 19832

[51] Int. Cl.² ............... H04N 3/14; H01L 27/14; H03B 1/00
[52] U.S. Cl. ................ 358/213; 358/167; 357/30; 328/162; 328/165; 307/221 D; 307/311; 250/578
[58] Field of Search ........... H04N/5/21; 358/36, 41, 358/167, 212, 213, 285; 328/162, 163, 165, 167; 250/211 R, 211 S, 578; 357/24, 30; 307/221 D, 311

[56] References Cited

U.S. PATENT DOCUMENTS

| | | | |
|---|---|---|---|
| 3,814,846 | 6/1974 | Snow | 358/213 |
| 3,946,151 | 3/1976 | Kamiyama et al. | 358/167 X |
| 4,011,402 | 3/1977 | Koike et al. | 358/213 |
| 4,045,817 | 8/1977 | Nakatani et al. | 358/213 |
| 4,067,046 | 1/1978 | Nakatani et al. | 358/167 X |

*Primary Examiner*—Robert L. Griffin
*Assistant Examiner*—Aristotelis M. Psitos
*Attorney, Agent, or Firm*—Stephen J. Limanek

[57] ABSTRACT

A noise reduction scheme for a photosensitive self scan system includes an array of photosensitive elements producing video signals and first and second pluralities of switching elements, one element of each of the pluralities of switching elements being connected to one photosensitive element of the array. A first video line connects each element of the first plurality of switching elements to a first input terminal of a summing device such as a differential amplifier and a second video line connects each element of the second plurality of switching elements to a second input terminal of the differential amplifier. Shift register means operated by clock pulses is provided to control the operation of each of the elements of the first plurality of switching elements to sequentially couple the photosensitive elements to the first input terminal and to apply periodically only clock pulse noise signals through the gate drain capacitance of the second plurality of switching elements to the second input terminal of the differential amplifier, so as to produce at the output of the amplifier a video signal substantially free of noise signals created by the clock pulses.

5 Claims, 3 Drawing Figures

PHOTOSENSITIVE SELF SCAN ARRAY WITH NOISE REDUCTION

BACKGROUND OF THE INVENTION

1. Field of the Invention

This invention relates to photosensitive self scan arrays and more particularly to a device and a circuit for eliminating noise induced by clock signals and switching devices, in such arrays.

2. Description of Prior Art

The photosensitive self scan arrays using photosensitive semiconductor cells are well known in the art. Such arrays use as photosensitive cells, phototransistors or photodiodes operating in storing mode. The cells, when one of their junctions is reverse-biased, are equivalent to a capacitor mounted in parallel with a current source. In normal operation, when the junction has been reverse-biased and set in open circuit, it discharges slowly due to a small recombination of the holes and electrons. Should the junction be illuminated, then it discharges quickly due to the generation of additional electrons and holes. The current generated by the discharge at the junction is a function of the light impinging the junction. This phenomenon is used in the photosensitive arrays for detecting the quantity of light impinging one or several photosensitive cells. For this purpose, all the photosensitive cells are initially charged, then submitted to a light pattern to be studied. The junction of each cell will discharge more or less, according to the quantity of light received. In a third step, the cells are recharged, the recharge current of each cell being a function of the lighting applied to the junction of this cell. Processing this current allows the quantity of light received by the photosensitive cell to be determined. The operation of such devices is explained with more details in the following articles: "Charge Storage Lights the Way for Solid-state Image Sensors" by Gene P. Weckler, published in "Electronics" of May 1, 1967, pages 75 to 78, and "A new Self-scanned Photodiode Array" by R. H. Dyck and G. P. Weckler, published in "Solid State Technology" of July 1971, pages 37 to 42.

The photosensitive self scan arrays are currently used in various domains. For example, they are used as an optical reader. In this application, the photosensitive cells are assembled as a matrix and scan a document to be optically read. A sequential detection of the state of the various cells of the matrix is used for defining the quantity of light received by each of the cells at a given time and therefore, for determining the respective illumination of the document elementary parts. Detecting the cell state can be performed automatically by using a shift register, each stage of which controls a photosensitive cell. A scanning start pulse is sent to the register input and propagates from stage to stage, controlling the sequential detection of the cell state. The propagation of the scanning start pulse is controlled by clock pulses and the detection of the cell state is controlled by switching devices such as transistors respectively associated to the register stages, each switching device being conditioned when the array stage associated with it receives in the same time the scanning pulse and the clock pulse.

One of the major problems involved in the operation of the photosensitive arrays lays in the parasitic noise signals added to the photosensitive cell detecting current. In effect, the discharge of the cells and therefore the recharge or detecting current, is extremely low and is heavily affected by the parasitic signals or noise generated, in particular, by the switching devices. It follows that, in the conventional photosensitive arrays, the signal to noise ratio is low, which does not allow a good optical reading.

Several solutions have been proposed to reduce the amplitude of the parasitic signals and to increase the signal to noise ratio. One of these solutions consists in feeding a differential amplifier, on the one hand, with a recharge current called "video signal" to which the parasitic signals are added and, on the other hand, with the parasitic signals themselves.

Then, the differential amplifier output delivers only the video signal. The noise line which feeds the differential amplifier and contains only the parasitic signals, receives the clock signals used in the photosensitive array, through very small capacitors set according to the components of the array itself and more particularly, to the switching devices. The capacitance of these capacitors is set so that the signals on the noise line, are equivalent to the noise signals affecting the video signal. This device does not take into account the fact that the noise signals disturbing the photosensitive array, are not constant in time. It follows that the signals on the noise line, do not correspond to the noise signals affecting the video signal. The differential amplifier output does not deliver a pure video signal and the optical reading performed by the photosensitive array is affected for it.

SUMMARY OF THE INVENTION

One of the objects of this invention is to overcome the above indicated disadvantages and to provide a photosensitive array unaffected by noise signals due to the capacitive effects of its components.

Another object of this invention is to provide an improved photosensitive array in which the video signal including noise signals, is fed to one of the inputs of a differential amplifier the second input of which receives the noise signals themselves.

Another object of this invention is to provide an improved circuit allowing to suppress the noise on the video line of a photosensitive array.

The foregoing and other objects, features and advantages of the invention will be apparent from the following more particular description of the preferred embodiments of the invention, as illustrated in the accompanying drawings.

DESCRIPTION OF THE PREFERRED EMBODIMENTS

Figure 1:
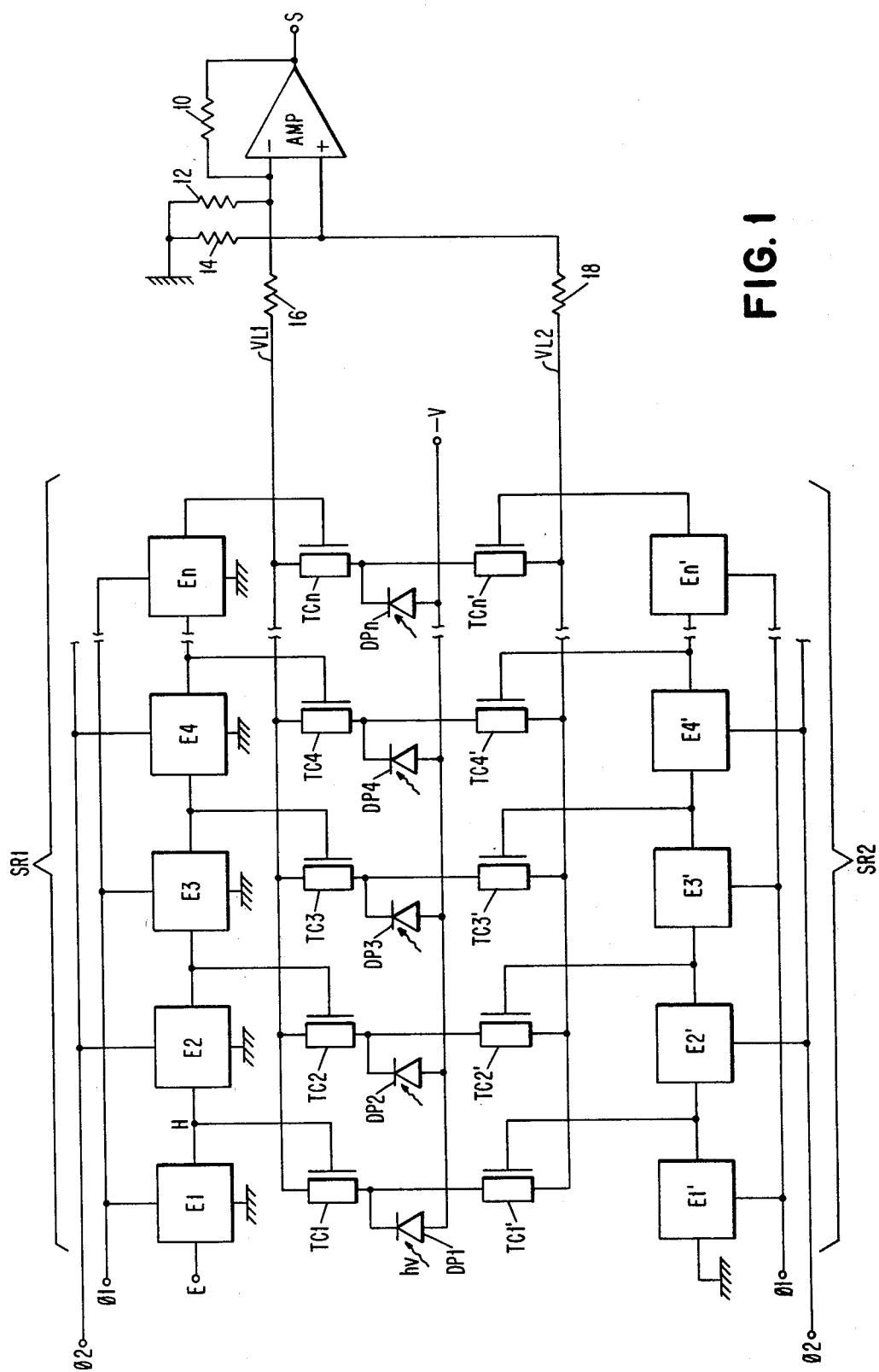
FIG. 1 shows a first embodiment of a photosensitive array according to this invention.

FIG. 1 shows a photosensitive array including n photosensitive cells DP1 to DPn to which are respectively associated, switching devices TC1 to TCn and stages E1 to En of a shift register SR1, which are conventionally assembled as known in the art. The shift register includes an input E to which is applied an input signal and each stage of this register is fed with clock pulses $\phi 1$ or $\phi 2$. Video line VL1 is connected in parallel to the output switching devices TC1 to TCn and carries the detecting currents of cells DP1 to DPn. This line VL1 feeds a first input of a differential amplifier AMP. This amplifier which is shown with its associated resistors, is well known in the art and its operation will not be described in detail. Photosensitive devices DP1 to DPn are biased to −V volts.

Also a second set of switching devices TC1' to TCn' and stages E1' to En' of a second shift register SR2 are respectively associated with each photosensitive cell. This second register includes an input connected to ground and each of its stages is provided with clock pulses $\phi 1$ or $\phi 2$ according to a pattern identical to the one of shift register SR1. The outputs of devices TC1' to TCn' are connected to video line VL2 which feeds the second input of the differential amplifier.

Figure 2:
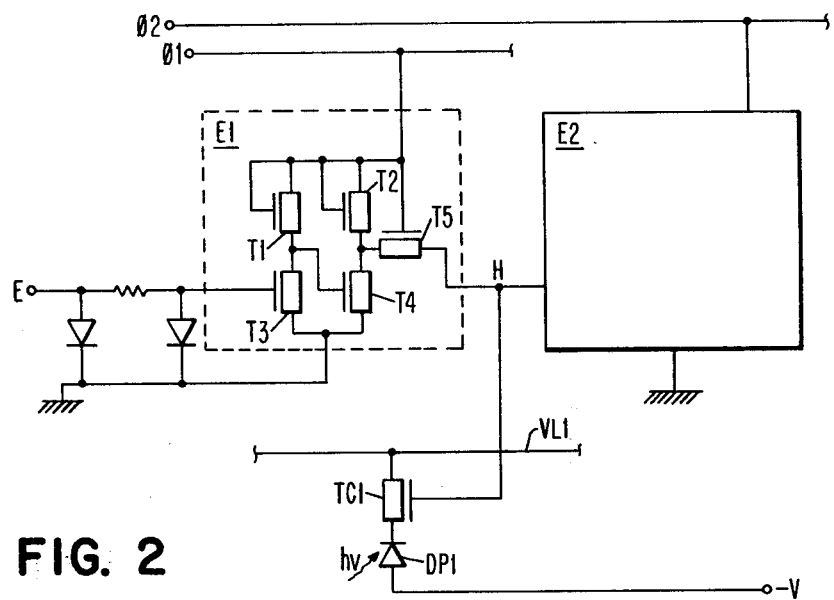
FIG. 2 is a more detailed illustration of a stage of the shift register used in the photosensitive array of FIG. 1.

In the assembly shown in the figures, the photosensitive cells are represented by photoelectric diodes but it should be understood that any component which can be charged by an appropriate biasing and which is conducting when receiving light to make its discharge easier, could be used. In the same way, components T1 to T5 forming the stages of the shift registers, as shown in FIG. 2, and the switching devices are represented by field effect transistors, but it would be possible to use any other technology using integrated or discrete components. Furthermore, to simplify the description, there are indicated two clock pulses $\phi 1$ and $\phi 2$ for respectively controlling stages E1, E3 and En and E2 and E4, of the shift registers. It is obvious that other patterns of clock pulses could be also used.

The operation of a photosensitive array including a shift register is well known in the art and is described, for example, in French Patent Application No. 74 31439 filed on Sept. 11, 1974, entitled: "Mode d'auscultation d'un ensemble photosensible" and having Application Publication No. 2284868, published Apr. 9, 1976. Before describing the operation of the device of this invention, the operation of a photosensitive array including only one shift register SR1 and only one set of switching transistors TC1 to TCn will be recalled, while referring to FIGS. 1 and 2.

Transistor TC1 controls the recharge, or biasing, or the isolation of diode DP1 as it is respectively conducting or not. It is controlled by a signal delivered to node H. This signal is generated by the application of a signal to E, which modifies the state of transistor T3, the modification being transferred to node H by transistors T4 and T5 as controlled by clock pulses, such as $\phi 1$, applied to transistors T1, T2 and T5. In addition, the signal delivered to node H changes the state of transistor T3 (not shown) of the following stage, which results in the transfer of the signal previously applied to E, to this stage. By applying this method, the register stages and therefore, the array photosensitive cells are processed in sequences, according to a given rate, each cell being recharged one time each sequence. Video line VL1 transfers the recharge or detection currents, called "video signals", to the differential amplifier, the output of which is processed to perform optical reading.

In such a photosensitive array, video line VL1 carries in addition to the video signals, noise signals which are mainly due to the capacitive effects of the switching transistors. As explained above, the noise signals disturb the video signal, which affects signal processing and optical reading.

The preponderant residual capacitance is formed by the drain-gate capacitance of switching transistors TC1 to TCn. When detecting the cell state, each of transistors TC1 to TCn is conditioned one after the other, as controlled by the detection clock signals of the photosensitive cell associated with the conditioned switching transistor to which are added the parasitic currents due to the drain-gate capacitances of all the other switching transistors which are blocked and connected to this video-line. But the gate voltage of these transistors is not stable, which is due in particular, to the secondary effects generated by the application of clock signals $\phi 1$ and $\phi 2$. Consequently, the parasitic currents generated by the drain-gate capacitances of the switching transistors, varies in time.

To counterbalance the parasitic effect due to these drain-gate capacitances, a second shift register SR2 substantially identical to the first register and embodied in the photosensitive array is provided symmetrically with respect to first register SR1. Switching transistors TC1' to TCn' are identical to transistors TC1 to TCn and respectively connect each stage of the second register to the array photosensitive cells. This connection is similar to the connection of the stages of the first register SR1 to cells DP1 to DPn through switching transistors TC1 to TCn. The drains of transistors TC1' to TCn' are connected to video line VL2. Since no signal is provided to the input of grounded shift register SR2 as indicated at E1', transistors TC1' to TCn' remain always blocked or turned off and no video signal appears on line VL2. This line receives only the noise signals due to the parasitic effects of the drain-gate capacitances of transistors TC1' to TCn'. These parasitic effects are identical or at least very similar to the ones generated by the drain-gate capcitances of transistors TC1 to TCn. Thus, video line VL1 carries the video signal itself plus the noise signals and line VL2 carries only the noise signals. Output S of differential amplifier AMP delivers a pure video signal substantially without any noise.

To obtain better results, it is recommended to embody, in the same manufacturing steps, SR1 and SR2 as well as switching transistors CT1 to CTn and CT1' to CTn', so that the capacitive effects on both video-lines, are substantially identical.

Figure 3:
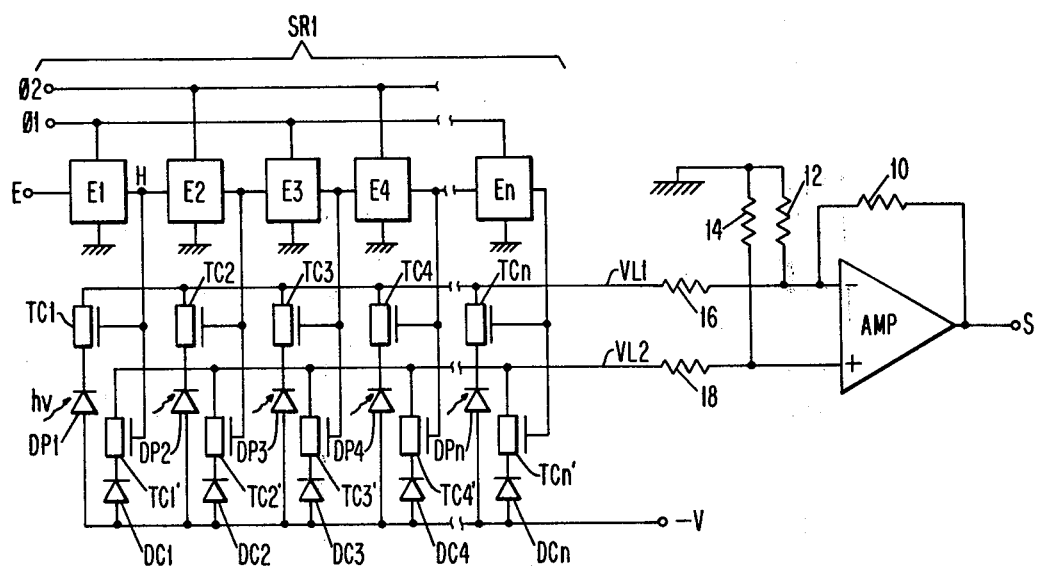
FIG. 3 shows a second embodiment of a photosensitive array according to this invention.

FIG. 3 illustrates another embodiment of this invention. The elements shown in this figure corresponding to the elements of FIG. 1, have the same references and operate as the ones shown in FIG. 1. Their operation will not be described again with reference to this figure. As shown in FIG. 3, shift register SR2 is removed and the electrodes of switching transistors TC1' to TCn' are connected as follows. The gate electrodes of transistors TC1' to TCn' are respectively connected to the gate electrodes of transistors TC1 to TCn. As shown in FIG. 3, the drain electrodes are connected to video line VL2 and the source electrodes are respectively connected through diodes DC1 to DCn to biasing voltage −V applied also to the photosensitive cells. Diodes DC1 to DCn are reverse-biased so that transistors TC1' to TCn' remain always blocked. It is to be noted that any other component operating as diodes DC1 to DCn in this example, could be used. The only requirement to be met is that these components should not be photosensitive.

As in the array of FIG. 1, the array shown in FIG. 3 includes a first video line VL1 receiving the video signal to which are added the noise signals and a second line VL2 carrying only noise signals. Output S of amplifier AMP delivers a relatively pure video signal unaffected by the noise. It is to be noted that the gate voltages of each transistor TC1 to TCn are respectively identical to the ones of transistors TC1' to TCn', since the gates of these transistors are connected together.

Therefore, the parasitic effect of the drain-gate capacitance of any transistor of the first set TC1–TCn is quite identical to the one of the transistor of the second set TC1'–TCn' associated to it.

While the invention has been particularly shown and described with reference to preferred embodiments thereof, it will be understood by those skilled in the art that various changes in form and details may be made therein without departing from the spirit and scope of the invention.

What is claimed is:

1. A photosensitive self scan system comprising
an array of photosensitive elements producing video signals,
first and second pluralities of switching elements, each element of each of said pluralities of switching elements being coupled to a respective one of said photosensitive elements,
a summing device having first and second input terminals,
a first video line coupling each element of said first plurality of switching elements to said first input terminal,
a second video line coupling each element of said second plurality of switching elements to said second input terminal,
first shift register means for producing control signals and first clock pulse noise signals, said control signals being coupled to said first plurality of switching elements for sequentially applying said video signals from said array of photosensitive elements to said first video line and said first clock pulse noise signals being coupled to said first plurality of switching elements for periodically applying said first clock pulse noise signals to said first video line, and
second shift register means for producing second clock pulse noise signals, said second clock pulse noise signals being coupled to said second plurality of switching elements for periodically applying said second clock pulse noise signals to said second video line in a known time relationship with respect to the application of said first pulse noise signals to said first video line,
whereby said video signals are produced at the output of said summing device and said clock pulse noise signals are suppressed within said summing device.

2. A photosensitive self scan system as set forth in claim 1 wherein said first and second pluralities of switching elements are field effect transistors and the outputs of said first shift register means are connected to the gate electrode of the transistors of said first plurality of switching elements with a first controlled electrode of said transistors of said first plurality of switching elements being connected to said photosensitive elements and a second controlled electrode of said transistors of said first plurality of switching elements being connected to said first video line, and the outputs of said second shift register means are connected to the gate electrode of the transistors of said second plurality of switching elements with a first controlled electrode of said transistors of said second plurality of switching elements being connected to said photosensitive elements and a second controlled electrode of said transistors of said second plurality of switching elements being connected to said second video line.

3. A photosensitive self scan system as set forth in claim 1 wherein said photosensitive elements are photosensitive diodes.

4. A photosensitive self scan system as set forth in claim 1 wherein said summing device is a differential amplifier.

5. A photosensitive self scan system as set forth in claim 1 wherein said second shift register means has applied to the input thereof, a reference potential signal.